US00PP36761P3

(12) United States Plant Patent
Reynbery

(10) Patent No.: US PP36,761 P3
(45) Date of Patent: Jun. 24, 2025

(54) ***CANNABIS* PLANT NAMED 'PTC8506V'**

(50) Latin Name: *Cannabis sativa*
Varietal Denomination: PTC8506V

(71) Applicant: Phylos Bioscience, Inc., Portland, OR (US)

(72) Inventor: Jared Reynbery, Portland, OR (US)

(73) Assignee: Phylos Bioscience, Inc., Portland, OR (US)

( * ) Notice: Subject to any disclaimer, the term of this patent is extended or adjusted under 35 U.S.C. 154(b) by 0 days.

(21) Appl. No.: 18/643,930

(22) Filed: Apr. 23, 2024

(65) Prior Publication Data

US 2024/0381800 P1 Nov. 14, 2024

(51) Int. Cl.
*A01H 5/00* (2018.01)
*A01H 6/28* (2018.01)

(52) U.S. Cl.
USPC ..... Plt./258
CPC ..... *A01H 6/28* (2018.05)

(58) Field of Classification Search
USPC ..... Plt./258
See application file for complete search history.

(56) References Cited

PUBLICATIONS

UPOV-PLUTO citation for 'PTC8506V'. retrieved from UPOV on Oct. 20, 2024. https://pluto.upov.int/result. 1 page. (Year: 2023).*

* cited by examiner

*Primary Examiner* — Karen M Redden
(74) *Attorney, Agent, or Firm* — Klarquist Sparkman, LLP

(57) ABSTRACT

A new and distinct variety of *Cannabis sativa* designated 'PTC8506V' as herein described and illustrated, characterized by elevated levels of THCV.

1 Drawing Sheet

Genus/species: *Cannabis sativa.*
Variety denomination: 'PTC8506V'.

BACKGROUND

*Cannabis* plants contain over a hundred known cannabinoids, which bind to endogenous endocannabinoid receptors. Varinolic cannabinoids, as known as varins, are a type of cannabinoid compounds having three carbon atoms in their alkyl side chain instead of the five carbon atom alkyl side chains more commonly associated with cannabinoids. Two such varins are tetrahydrocannabivarin (THCV) and cannabidivarin (CBDV), which are homologues of tetrahydrocannabinol (THC) and cannabidiol (CBD), respectively. Each varin has a unique pharmacological profile and distinct molecular targets.

THCV and CBDV have potential benefits across a broad set of applications. *Cannabis* plants or extracts with high THCV levels, for example, can be used as an agent for anticonvulsant activity, obesity-associated glucose intolerance, appetite suppression, anxiety management for PTSD, diabetic neuropathy, and major neuropathic and pain related pathologies. Another THCV application is that of an appetite suppressing compound. CBDV has been shown to have anti-epileptic and anticonvulsant activity.

Research and development as well as the sale of varin products has been limited due to low commonly occurring levels of varins in *Cannabis* flower. The ability to produce *Cannabis* with high varin levels will create a platform for a new Cannabinoid category with differentiated, high margin products in both medical and recreational markets. The present application solves these problems by providing a novel *Cannabis* plant having high THCV, which is referred to by the variety name 'PTC8506V'.

SUMMARY

The new variety of *Cannabis sativa* was created by sourcing *Cannabis* plants that produce THCV and THC. Crosses were conducted to elevate further THCV, THC and/or other varins. All breeding, cultivation, and chemotype analyses were conducted in Hillsboro, Oregon. 'PTC8506V' resulted from the cross of a high THC pollen receiver plant ('21GAQ-1271', unpatented) and a high THCV pollen donor plant ('21VLP5-1-102', unpatented). '21GAQ-1271' is a clonal variety with a THC content of 22.2%, and a THCV content below the limit of detection (LOD). '21GAQ-1271' has greenish-purple flowers with heavy trichome coverage, moderate density, and strong aroma. '21GAQ-1271' has an upright plant growth habit with moderately long internodes and matures in 8-9 weeks. '21VLP5-1-102' had a THC content of 1.2%, and THCV content of 5.66%. '21VLP5-1-102' flowers are greenish-purple with low trichome coverage, very low density, and moderately weak aroma. '21VLP5-1-102' has a moderately wide plant growth habit with very long internodes and matures in 10-12 weeks. A clone of '21VLP5-1-102' was crossed onto a clone of '21GAQ-1271' in 2021. 32 of the resulting F1 seed were sown. 'PTC8506V' was discovered and selected as a single plant from this F1 seed and was subsequently propagated clonally in Hillsboro, OR. 'PTC8506V' was asexually reproduced by apical and sub-apical semi-herbaceous stem cuttings in Hillsboro, Oregon for eight cycles. Asexual reproduction has demonstrated that 'PTC8506V' reproduces true to type with all of the characteristics, as herein described, and firmly fixed and retained through successive generations of asexual propagation.

The new variety is named 'PTC8506V' and is characterized as having elevated levels of THCV. In comparison to its parents, 'PTC8506V' has higher THCV (relative to either parent), and higher THC relative to the pollen donor plant. 'PTC8506V' can additionally be distinguished from either parent at least based on the characteristics provided in Table 1.

TABLE 1

Comparison to Parent Varieties.

| Variety | Trichome Coverage | Aroma Strength | Aroma Type | Growth Habit | Inter-node | Maturity Time |
|---|---|---|---|---|---|---|
| '21GAQ-1271' | Heavy | Strong | Sweet cookies, earth, garlic | Upright | Moder-ately long | 8-9 weeks |
| '21VLP5-1-102' | Low | Moder-ately weak | Grass, earth, citrus | Moder-ately wide | Long | 10-12 weeks |
| 'PTC8506V' | Moderate | Moder-ately strong | Pine, earth, fuel, and a slight fruiti-ness | Upright | Moder-ately long | 8-10 weeks |

BRIEF DESCRIPTION OF THE PHOTOGRAPH

FIG. 1 is a photograph of a flowering plant of 'PTC8506V' that is approximately 83 days old, growing in Hillsboro, Oregon.

DETAILED BOTANICAL DESCRIPTION

The following is a detailed description of the new *Cannabis* variety 'PTC8506V'. Unless otherwise indicated, all color designations provided herein are hex color codes.

All breeding, cultivation, and chemotype analyses were conducted in Hillsboro, Oregon.

*Cannabis* plants having elevated THCV or THC levels were sourced and obtained, and crosses were conducted to produce new varieties to further elevate THCV and THC levels. The plants were crossed to produce new varieties having elevated THCV and THC levels. Plant variety 'PTC8506V' was selected and asexually reproduced.

Table 2 describes the general characteristics of 'PTC8506V' at 55 days after lighting was changed to 12 hours on/12 hours off.

TABLE 2

| | |
|---|---|
| Plant life forms | An herbaceous plant (herb) |
| Plant growth habit | An upright, tap-rooted annual plant, forming fibrous roots when asexually propagated |
| Plant origin | A controlled cross between pollen acceptor ('21GAQ-1271') and pollen donor plant ('21VLP5-1-102). |
| Plant propagation | Asexually propagated by apical and sub-apical semi-herbaceous stem cuttings |

TABLE 2-continued

| | |
|---|---|
| Propagation Ease | Easy |
| Plant shape | Simple erect |
| Height | 117 cm to 121 cm |
| Width | 87 cm to 101 cm |
| Time to harvest | 10-12 weeks |
| Resistance to pests or diseases | Unknown |
| GMO? | No |

Table 3 describes the leaf/foliage of 'PCT8506V'. Color codes are hex color codes.

TABLE 3

| | |
|---|---|
| Leaf Arrangement | Alternate |
| Leaflet Type | Palmately compound |
| Leaflet Structure | Serrated margins, lightly acicular to lanceolate leaflets, tapering to an acuminate apex |
| Leaflet Margins | Jaggedly serrate with each tooth apex angled toward leaflet apex |
| Leaf hairs | Present on both upper and lower surfaces |
| Leaf length with petiole at maturity | 18.5 cm to 23 cm |
| Petiole length at maturity | 6 cm to 9.5 cm |
| Petiole diameter at maturity | 1.9 mm to 2.5 mm |
| Petiole color | #6B4247 |
| Anthocyanin color and intensity in Petioles | #F9CCC5. Medium intensity in vegetative stage; stronger in flowering stage |
| Stipule length at maturity | 6.2 mm to 6.8 mm |
| Stipule shape | Linear with slight curvaceous growth |
| Stipule color | #3C4D03 |
| No. of leaflets | 3 to 7 |
| Middle largest (longest) leaflet length | 12 cm to 17.5 cm |
| Middle largest (longest) leaflet width | 2.5 cm to 3.1 cm |
| Middle largest (longest) leaflet length/width ratio | 3.8 to 4.8 |
| No. teeth of middle leaflet | 28 to 34 |
| Leaf (upper side-adaxial) color | #35530A |
| Leaf (lower side-abaxial) color | #35530A |
| Leaf glossiness | Matte |
| Vein/midrib shape | Obliquely continuous throughout leaflet |
| Vein/midrib color | #E6DAA6 |
| Aroma | Earthy notes of pine, fuel, and a slight fruitiness |

Table 4 describes the stem of 'PTC8506V'.

TABLE 4

| | |
|---|---|
| Stem shape | Hollow, ribbed, texture |
| Stem length | 117 cm to 121 cm |
| Stem strength | Strong and upright |
| Stem diameter at base | 13.6 mm to 14.5 mm |
| Stem color | #373E02 |
| Depth of main stem ribs/grooves | Shallow |
| Internode length | 3 cm to 9.5 cm |

Table 5 describes the inflorescence of 'PTC8506V'.

TABLE 5

| | |
|---|---|
| Inflorescence type | Elongated compound cymes |
| Flowering (blooming) habit | Natural flowering season is Autumn in Hillsboro, Oregon. |
| Proportion of female plants | 100% pistillate |
| Inflorescence position | Terminal and axillary |

TABLE 5-continued

| | |
|---|---|
| Number of inflorescences produced per plant | 100 to 150 |
| Flower arrangement | Cymose |
| Length of inflorescences | 3 cm to 3.8 cm |
| Numbers of flowers per plant | Hundreds to thousands flowers per plant, multitudinous, congested with high concentrations on bushier wide inflorescence |
| Flower shape | Urceolate |
| Flower (individual pistillate) length | 5.1 mm to 5.3 mm |
| Flower (individual pistillate) depth | 2 mm |
| Flower (compound cyme) diameter | 5.5 cm to 8 cm |
| Corolla | No defined corolla |
| Corolla color | N/A |
| Bract shape | Urceolate |
| Bract color | #4B5D16 |
| Typical bract numbers | 3 to 200 bracts per inflorescence. |
| Bract length | 3 mm to 5mm |
| Bract width | 2.3 mm to 2.7 mm |
| Bract apex and base description | Bracts have a rounded base and caudate apex. |
| Bract Texture | Bract texture is smooth and covered with sticky trichomes. |
| Bracteole number, shape, length, width, apex, margin, base descriptors, texture, and color | Bracteoles are not present |
| Calyx shape | No defined calyx |
| Calyx color | N/A |
| Pistil number per flower | One |
| Pistil color | Pistil consists of the stigma, style, and ovary and cannot be given a single color. |
| Stigma shape | Acute |
| Number of stigmas per flower | Two |
| Stigma length | 4.6 mm to 6.5 mm |
| Stigma color | #373E02 |
| Trichome shape | Capitate-stalked glandular |
| Trichome color | #F1E7E2 |
| Terminal inflorescence shape | Oblong |
| Terminal inflorescence color | #B7E1A1 |
| Terminal inflorescence length | 12.5 cm to 14 cm |
| Terminal inflorescence width | 5 cm to 6.5 cm |
| Pedicel | Absent |
| Peduncle length | 6.8 mm |
| Peduncle diameter | 4.1 mm |
| Peduncle texture | Lightly ribbed |
| Peduncle color | #9BB53C |
| Staminate shape | No staminate flowers produced naturally; however, male flower (staminate) can be induced with stress or ethylene-blocking compounds |
| Sepal color | N/A |
| Pollen description | N/A |
| Petal description | Apetalous |

Table 6 describes other characteristics of 'PTC8506V'

TABLE 6

| | |
|---|---|
| Time period and condition of flowering/blooming | 8 to 10 weeks |
| Proportion of hermaphrodite plants | Lower (<5%) in clones |
| Hardiness of plant | Hardy to tolerate of warm and dry conditions without showing stress. Not tolerant to soil oversaturated with water for long periods |

Chemical analyses were conducted using High Performance Liquid Chromatography to detect the cannabinoids described herein. Table 7 describes a chemotype analysis of 'PTC8506V', which was chemotyped by taking a sample from the main cola at day 56 after initiation of the 12:12 light cycle, which initiates flowering. Trichomes were 70% cloudy and 5% amber, indicative of full maturity at sampling.

TABLE 7

| Cannabinoid and other chemicals | % wt |
|---|---|
| Total THC | 4.613 |
| Total THCV | 11.067 |
| Total CBG | 0.047 |
| Total CBD | <LOD |
| Total CBC | <LOD |
| Total CBGV | <LOD |
| Total CBDV | <LOD |
| alpha-Pinene | 0.057 |
| Camphene | 0.011 |
| beta-Myrcene | 1.557 |
| beta-Pinene | 0.098 |
| delta-3-Carene | <LOQ |
| alpha-terpinene | <LOQ |
| D-Limonene | 0.211 |
| beta-Ocimene | 0.275 |
| p-Cymene | <LOQ |
| Eucalyptol | <LOQ |
| gamma-Terpinene | <LOQ |
| Terpinolene | <LOQ |
| Linalool | 0.003 |
| Isopulegol | <LOQ |
| Geraniol | <LOQ |
| beta-Caryophyllene | 0.05 |
| alpha-Humulene | 0.0227 |
| Nerolidol 1 | <LOQ |
| Nerolidol 2 | 0.011 |
| Guaiol | <LOQ |
| Caryophyllene Oxide | 0.011 |
| alpha-Bisabolol | 0.026 |
| Total Terpenes | 2.315 |

What is claimed is:

1. A new and distinct variety of *Cannabis sativa* designated 'PTC8506V' as herein described and illustrated.

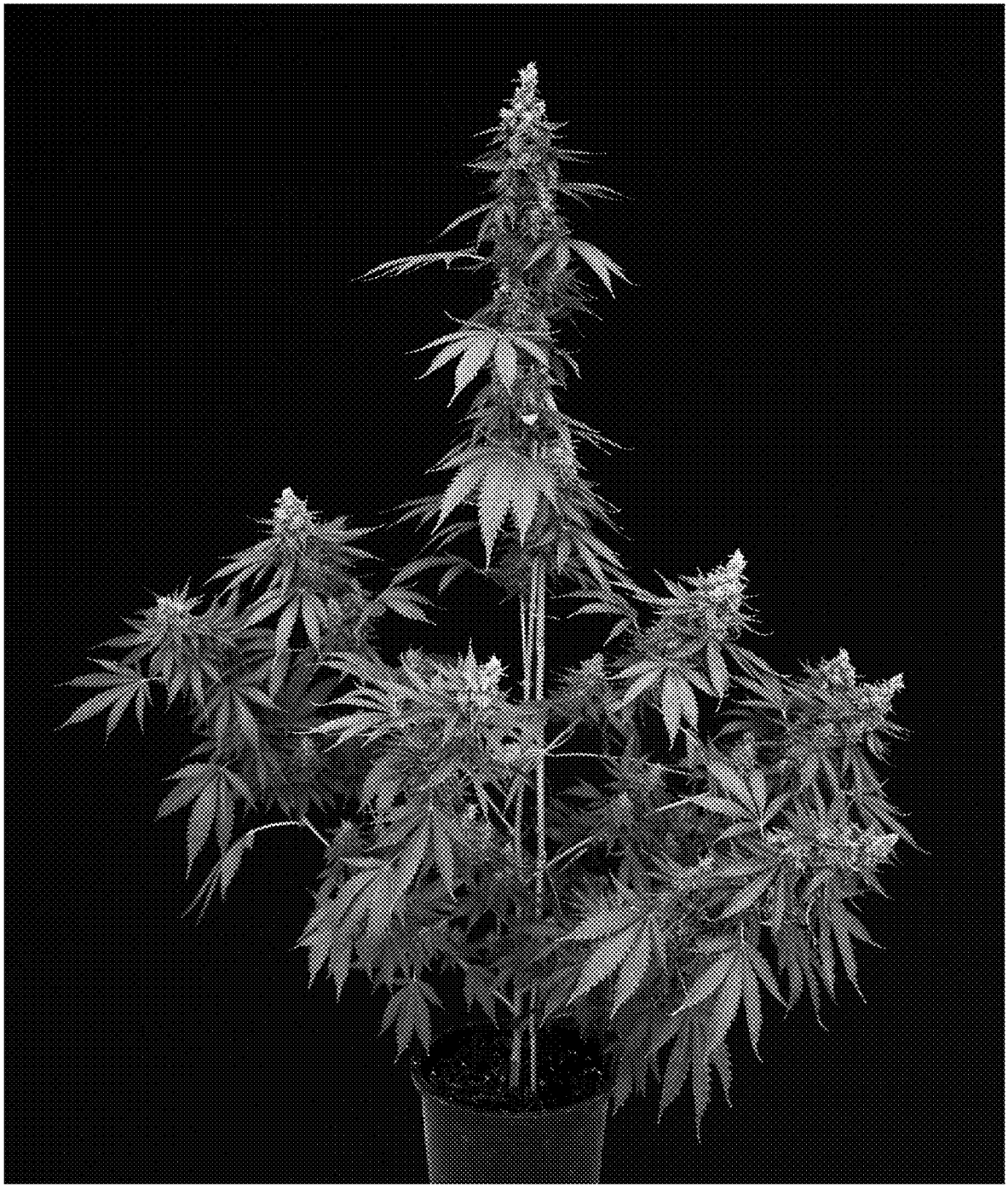

* * * * *